United States Patent
Pachl et al.

(10) Patent No.: US 7,758,812 B2
(45) Date of Patent: Jul. 20, 2010

(54) ANALYSIS SYSTEM FOR DETERMINING AN ANALYTE CONCENTRATION, TAKING INTO CONSIDERATION SAMPLE-AND ANALYTE-INDEPENDENT LIGHT-INTENSITY CHANGES

(75) Inventors: Rudolf Pachl, Ellerstadt (DE); Joachim Hoenes, Zwingenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1666 days.

(21) Appl. No.: 10/499,252

(22) PCT Filed: Dec. 19, 2002

(86) PCT No.: PCT/EP02/14534

§ 371 (c)(1),
(2), (4) Date: Aug. 24, 2004

(87) PCT Pub. No.: WO03/056314

PCT Pub. Date: Jul. 10, 2003

(65) Prior Publication Data

US 2005/0054082 A1 Mar. 10, 2005

(30) Foreign Application Priority Data

Dec. 22, 2001 (DE) .............................. 101 63 775

(51) Int. Cl.
*C12M 1/34* (2006.01)
(52) U.S. Cl. ................. 422/82.05; 422/82.09; 436/164; 436/172
(58) Field of Classification Search .............. 422/82.05, 422/82.07, 82.08, 82.09; 436/164, 171, 172
See application file for complete search history.

(56) References Cited

U.S. PATENT DOCUMENTS

| 4,238,565 A | 12/1980 | Hornby et al. | ................. 435/7 |
| 4,373,818 A | 2/1983 | Yamamoto et al. | .......... 356/408 |
| 5,356,780 A | 10/1994 | Robinson et al. | ............. 435/7.6 |

(Continued)

FOREIGN PATENT DOCUMENTS

DE 30 40 512 A1 4/1981

(Continued)

OTHER PUBLICATIONS

Jose F. Sierra, Javier Galban, and Juan R. Castillo, "Determination of Glucose in Blood Based n the Intrinsic Fluorescence of Glucose Oxidase," *Analytical Chemistry*, vol. 69, No. 8, (Apr. 15, 1997); pp. 1471-1476.

(Continued)

*Primary Examiner*—Robert J Hill, Jr.
*Assistant Examiner*—Dwan A Gerido
(74) *Attorney, Agent, or Firm*—Justin L. Sage; Roche Diagnostics Operations, Inc.

(57) ABSTRACT

The invention concerns an analytical system and a method for determining an analyte which ensures an exact determination by correcting the measured values based on sample- and analyte-independent light intensity changes. The invention takes into account light intensity changes which are based on changes of measurement conditions in the apparatus. The invention is particularly suitable for use in analytical systems for glucose determination in which light-conducting test elements are used.

19 Claims, 2 Drawing Sheets

U.S. PATENT DOCUMENTS

Figure 1:
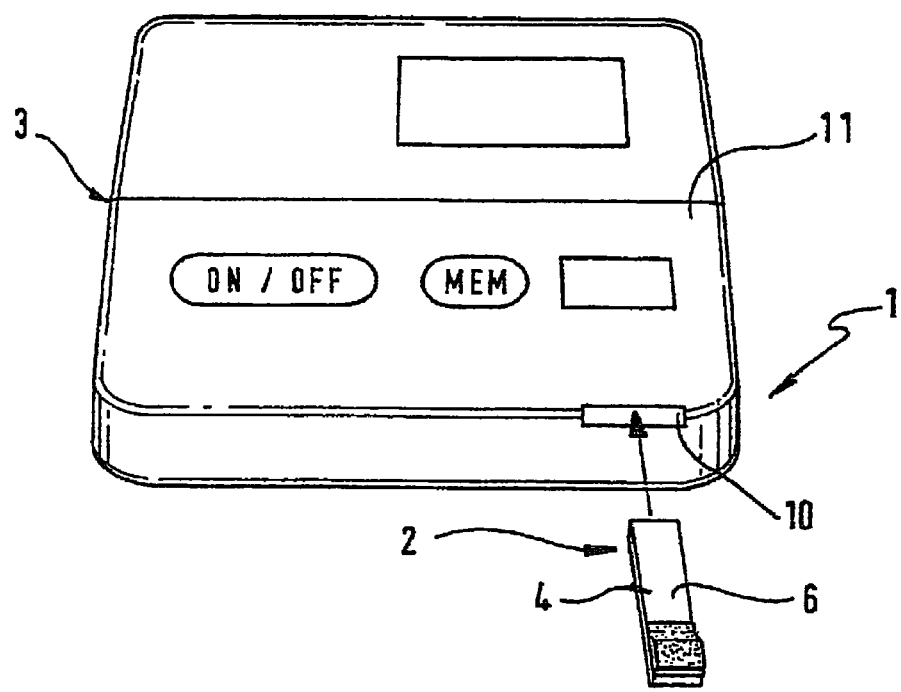

| | | | |
|---|---|---|---|
| 5,592,290 A | | 1/1997 | Arai et al. |
| 5,674,699 A | * | 10/1997 | Saunders et al. ............ 435/7.93 |
| 5,792,662 A | * | 8/1998 | Hayashi et al. ................. 436/8 |
| 5,795,543 A | | 8/1998 | Poto et al. ................. 422/82.05 |
| 6,036,919 A | | 3/2000 | Thym et al. .................... 422/58 |
| 6,268,162 B1 | | 7/2001 | Phillips et al. ................. 435/14 |

FOREIGN PATENT DOCUMENTS

| | | |
|---|---|---|
| DE | 41 28 846 A1 | 3/1993 |
| EP | 0 247 439 B1 | 2/1990 |
| EP | 0 431 456 B1 | 11/1990 |
| EP | 0 618 443 B1 | 3/1994 |
| EP | 0 816 849 B1 | 3/2001 |
| EP | 0816849 * | 3/2001 |
| GB | 2 188 728 A | 10/1987 |
| JP | 63101757 | 5/1988 |
| JP | 8-20364 | 3/1996 |
| JP | 10505676 T | 6/1998 |
| WO | WO 96/07908 A1 | 3/1996 |
| WO | WO 01/48461 A1 | 7/2001 |
| WO | WO 01/48464 A1 | 7/2001 |

OTHER PUBLICATIONS

Daniela D. Schlereth and Rob P.H. Kooyman, "Self-assembled monolayers with biospecific affinity for NAD (H)-dependent dehydrogenases: characteriszation by surface plasmon resonance combined with electrochemistry 'in situ'," *Journal of Electroanalytical Chemistry*, 444 (1998) pp. 231-240.

Gyles E. Cozier, Raff A. Salleh and Christopher Anthony, "Characterization of the membrane quinoprotein glucose dehydrogenase from *Escherichia coli* and characterization of a site-directed mutant in which histidine-262 has been changed to tyrosine," *Biochemical Society*, (1999) pp. 639-647.

* cited by examiner

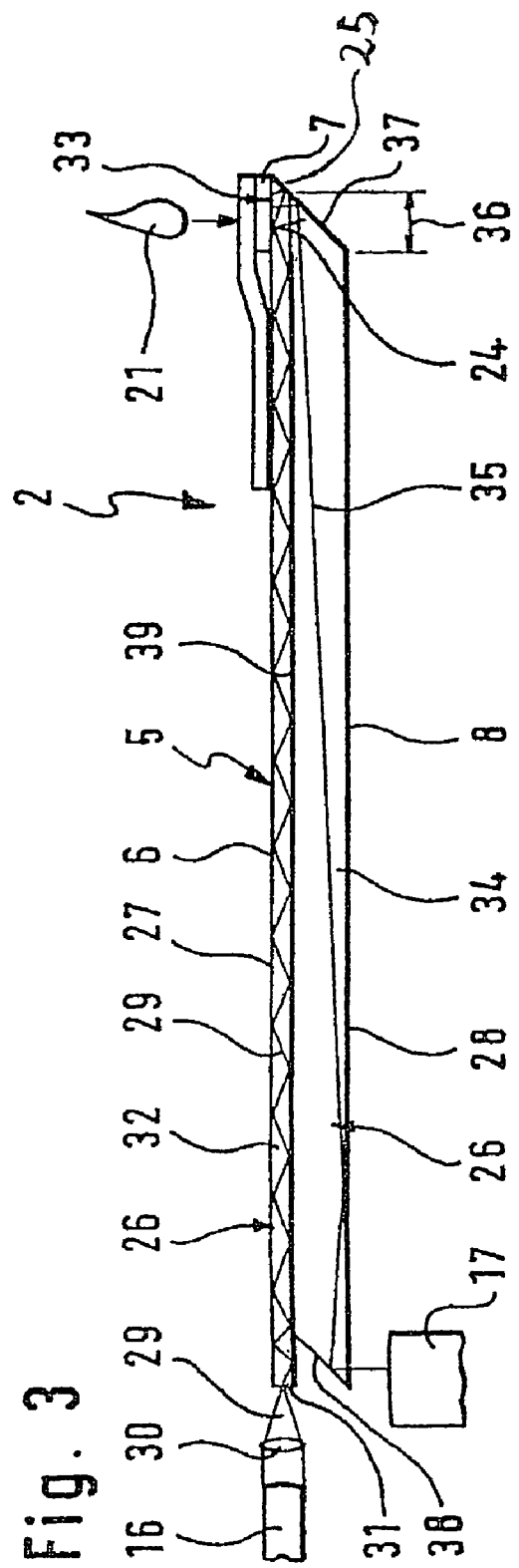

ANALYSIS SYSTEM FOR DETERMINING AN ANALYTE CONCENTRATION, TAKING INTO CONSIDERATION SAMPLE-AND ANALYTE-INDEPENDENT LIGHT-INTENSITY CHANGES

The present invention is in the field of sample liquid analysis using analyte-specific, disposable test elements.

Analytical systems which use disposable test elements are commonly used in the prior art especially for determining the blood sugar level. These instruments are used to monitor the blood sugar level of diabetics so that this can be used as a basis for adjusting eating behaviour or insulin administration.

In this field there are so-called sensor measuring devices which determine blood glucose on the basis of an electrochemical measurement and optical systems in which an analyte-dependent color change on the test element is used to determine the analyte concentration.

Photometric or reflection-photometric evaluation of test elements are methods that are frequently used to rapidly determine the concentration of analytes in samples. Test elements that are evaluated by photometry or reflection photometry are of major importance especially for determining blood glucose in capillary blood.

Although such photometric or reflection-photometric evaluations are used especially in the field of medical diagnostics, they are for example also commonly used in the field of environmental analysis. Other examples of the use of optical systems that are based on an analyte-dependent color change are urine test strips and test elements for other parameters such as lactate, creatinine, protein, uric acid, leucocytes.

In order that the analyte to be determined is checked as regularly as possible, such analytical systems have also been designed for the home monitoring field.

Common home monitoring analytical systems for determining the blood glucose content which can be operated by the patients themselves comprise test elements on which an analytical area is arranged which is contacted with the blood of the patient.

The test element is inserted into the instrument by the user. An optical change which depends on the analyte concentration is detected by a suitable optical measuring system utilizing the light reflected or transmitted from the test element such that the concentration of the blood sugar can be determined. Such a system is described for example in the document EP B 0 618 443. Moreover such instruments are commercially available e.g. under the names Accutrend®, Accu Check®, Glucotrend® and Glucometer®.

The composition of such test elements is described for example in the document U.S. Pat. No. 6,036,919.

A general trend in performing analytical tests is to achieve precise results that are independent of interfering non-analyte-dependent effects despite small amounts of sample. This is of major importance especially in the field of blood sugar determination since only small amounts of sample are available in this case.

Interfering effects on light intensity are for example caused by non-constant apparative measuring conditions and by sample components in the analytical system which have effects on the amount of light registered by a detector. Such analyte-independent changes in light intensity falsify measurement results such that for example an erroneous glucose concentration is determined.

It has turned out that changes of the measuring conditions in the apparatus play a major role especially in some fields of application and result in considerable errors in the concentration determination of the analyte. Reasons for sample-independent changes of the measuring conditions in the apparatus are for example incompletely darkened detection and/or measuring areas resulting in detection of ambient light by the detector. Furthermore, variations in the measuring conditions can be caused by fluctuations in the output of optical components such as the illumination unit or the detector due to aging effects or soiling.

In special analytical systems such as those used in the field of glucose measurement, the test element contains light-conducting elements and thus forms a part of the illumination unit. In such test elements the light is coupled into and through the light-conducting elements of the test element and the transmitted or reflected light is coupled out again. Variations for example in the manufacture of the test elements, differences in the coupling of the test elements to the optical system of the instrument or soiling, to mention only a few factors, considerably influence the measuring results.

The detection of changes in the measuring conditions caused by the apparatus in analytical systems which determine the analyte concentration based on light absorption is described in the prior art in the U.S. Pat. No. 4,373,818. In the said patent a light intensity of the analytical system is measured when the illumination unit is switched off so that the detector registers the ambient light.

In the above-mentioned examples of medical analytical systems, measurements are often carried out within an open measuring chamber and hence ambient light is preferably registered and compensated according to U.S. Pat. No. 4,373,818 on the basis of the instrument design. However, under these conditions no allowance is made for any remaining changes in the measuring conditions that are for example due to the test element. However, especially when using test elements having light-conducting properties, the light-conducting capability of such test elements can be impaired to such an extent that an extensive error correction is required.

The object of the invention is to determine inconstant measuring conditions caused by the apparatus of an analytical system which determines the analyte concentration on the basis of absorption measurements and to take them into account in order to correct the measured value.

The invention enables a correction of errors due to inconstant apparatus-related measuring conditions within an analytical system. In addition a preferred embodiment of the invention also enables the determination of sample-dependent changes in light intensity in addition to variations in the measuring conditions of the apparatus. Consequently the invention allows a more exact calculation of analyte concentrations based on light absorption by the analytes which takes into account a change in analyte-independent measuring conditions.

The analytical system comprises a test element which has a light absorption in a first wavelength range before sample application that is previously known and is not equal to zero, an illumination unit which emits at least two different wavelength ranges and irradiates the test element, a detector unit which is positioned such that transmitted or reflected light of the test element is registered and an evaluation unit that is used to determine a correction value from an analyte-independent absorption of the test element in the first wavelength range and to determine a measured value from an analyte-dependent absorption of the test element in a second wavelength range. The concentration of the analyte is determined by the evaluation unit with a correction of the measured value taking into account the correction value.

Illumination units in the sense of the invention are those that have an essentially continuous emission spectrum e.g. glow lamps as well as those that have a so-called band spectrum e.g. light emitting diodes. Light-emitting diodes are particularly suitable for use in a portable analytical system since they have a relatively high degree of effectiveness which is important for battery-operated devices. Furthermore light-emitting diodes are available for a series of wavelength ranges in the visible and infrared range. In principle the light sources known in the prior art for diagnostic detection systems are suitable. Wavelength ranges that can be used within the scope of the invention also include UV and IR in addition to the visual range.

Test elements in the sense of the invention are used for sample application such that an analyte in a sample can be determined by the analytical system where the test element is designed such that it has an absorption in a first wavelength range that is previously known and is not equal to zero. Test elements in the sense of the invention are usually strip-shaped. An absorbent support material is preferably mounted on a holder that is used for handling. A reagent layer which reacts with the analyte is for example located in one detection zone of the support material i.e. the test field. The sample that is contacted with the detection zone results in a detectable change in the test field in the test element. In a large number of analytical methods, the analyte reacts with the reagent layer which is for example composed of a heteropoly acid which is reduced by the analyte to form the dye diheteropoly blue. The formation of the dye is dependent on the analyte concentration and is detected as a change of the test field in the visible range of the spectrum. In a preferred embodiment the analyte is an electron-rich aromatic amine or is converted into such an amine by a substance. Such a substance can for example be a nitrosoaniline derivative which, in a preferred embodiment, has a previously known absorption in a first wavelength range. The detection of analyte concentrations on the basis of a reaction of the analyte with a reagent system is described for example in the patent EP 0431456 B1.

The test element is subject among others to certain manufacturing tolerances which can cause measuring errors.

Furthermore differences in the intensity of the illumination of the test element edge and light scattering on dust or other soiling of the test element are only a few examples that are additionally responsible for measuring errors due to a varying quality of the test elements.

As already mentioned apparatus-related measuring errors occur particularly frequently when using light-conducting test elements. Within the scope of the invention such test elements can comprise a light-conducting layer in which preferably total reflection occurs. Light is coupled into the test elements through an entry surface which is preferably formed by a cut surface at the front end of the light-conducting layer. In order to couple the light out, the refractive index of the light-conducting layer can be changed in the area of the detection zone in such a manner that total reflection no longer occurs. In addition it is also possible to couple out the light by means of a suitable light guide within a light-conducting layer. Possible embodiments of light-conducting test elements are described in the patent application WO 01/48461.

Variations in the measuring conditions caused by light-conducting test elements (e.g. by manufacturing tolerances in the test elements or by variations in the coupling of the light-conducting test element to the optical system of the instrument) are detected by the analytical system according to the invention and thus a correction according to the invention proves to be particularly advantageous when using light-conducting test elements.

The well-known detectors and especially semiconductor detectors of the prior art can be used within the scope of the present invention. It is important to select the detector or detectors such that radiation reflected from the detection zone or transmitted through the detection zone results in a signal when the detector is illuminated with this radiation. Detectors can be advantageously used which have a sensitivity maximum in the range of the reflected or transmitted radiation. Filters may also be optionally used which selectively allow the measuring radiation to pass through in order to make the detection more stable towards the effects of interfering light.

The use of filters is necessary especially when using illumination units with a continuous emission spectrum. The filters can either be a requirement of the illumination unit or the detector in order to enable a selection of the desired wavelengths.

The evaluation unit of the analytical system comprises a module for error correction which can for example be in the form of an operation amplifier. The evaluation unit registers the counts generated in the detector which depend on the light intensity as a measure for a relative light intensity. The evaluation unit calculates an absolute light intensity by relating the registered counts to a reference quantity e.g. the white value whose registered counts are set at 100% of the light intensity and corrects this light intensity as described.

The concentration can for example be determined from the light intensity with the aid of calibration curves. The use of calibration curves to determine concentrations is described for example in the document EP 0 247 439.

The analytical system preferably comprises an evaluation unit which additionally determines the light intensity detected by the detector in the second or in a third wavelength range where essentially no absorption by the test element takes place in this wavelength range.

The absorption values in a third wavelength range or in the second wavelength range which is the wavelength range in which essentially no absorption takes place is referred to as the white value. If this white value is preferably measured in the second wavelength range which is equal to that for the analyte, the measurement is carried out on the test element before the sample is applied. Consequently no additional optical system for a wavelength range has to be provided in order to determine the white value.

The evaluation unit calculates the measured value taking into consideration the white value such that, in addition to determining the correction value, an additional error correction takes place.

The correction value of the analytical system which is measured in the first wavelength range can for example be determined using a dry test element which advantageously absorbs more than 50% of the light, preferably more than 80% and especially essentially completely (ca. 100%) absorbs the light. A complete absorption of the dry test element proves to be advantageous since this minimizes the error for subsequent calculation steps. Hence the evaluation unit can detect or calculate the amount of light registered by the detector in this wavelength range despite 100% light absorption of the test element. This measured value is referred to as the black value since no light would be detected if the measuring apparatus behaves ideally. This means that in the case of real behaviour the amount of light is registered which is a priori not absorbed by the test element and changes thereof are for example influenced by soiling of the test element, ambient light, differences in the quality of the test elements etc.

In a preferred embodiment the previously known absorption in the first wavelength range is caused by an absorber such as tartrazine present in the test element which does not interact with the sample and thus guarantees a previously known absorption for example even after sample application.

The test elements advantageously have a light-conducting element and are coupled to an illumination unit so that they represent a part of the illumination unit.

However, the correction value can also be measured on a wet test element after sample application. Under these conditions the amount of light is detected which is registered by the detector when the absorption of the test element is previously known and there is an additional sample-dependent absorption in the first wavelength range. Consequently a correction of the measured value by this correction value additionally takes into account the analyte-independent influence of the sample in the first wavelength range (e.g. intrinsic sample color, change of the refractive index caused by wetting) in addition to changes in apparatus-related measuring conditions.

In a preferred embodiment the evaluation unit registers at least two correction values where the absorption of the dry test element before sample application and the absorption of the wet test element after sample application is determined in the first wavelength range.

The proportion of the absorption in the first wavelength range which is sample-dependent and analyte-independent and is not influenced by the measuring conditions of the apparatus is determined by comparing the determined correction values. In the correction of the measured value, the sample-dependent light intensity change in the second wavelength range is deduced from the sample-dependent light intensity change in the first wavelength range. In this connection the change in light intensity in the first wavelength range caused by the sample can be set to be essentially equal to the sample-dependent change in light intensity in the second wavelength range. However, it is also possible to determine the sample-dependent light intensity change in the second wavelength range by for example extrapolation using the evaluation unit.

In the prior art it is known that different wavelength ranges can be used to correct the concentration determination in an analytical system but these measurements are not used to determine a black value.

On the one hand, the measurement is carried out in the prior art in a first wavelength range in which the test element does not absorb or does not substantially absorb and hence a white value of the system is determined. On the other hand, measurements in a first wavelength range result in the determination of the influence of the sample on the analytical result since blood pigment present in the sample causes an additional absorption in the measurement. The absorption of the blood pigment in the second wavelength is extrapolated from the absorption of the blood pigment in the first wavelength range (EP-A3-0 816849).

A black value as defined above is not taken into account in the above corrections. However, within the scope of the invention a correction for the white value and/or the influence of sample can additionally be taken into consideration in addition to correcting the measured values for the black value.

The invention additionally concerns two methods for detecting non-analyte-related light intensity changes in analytical systems.

One method comprises irradiating a test element before sample application and detecting the light reflected or transmitted from the test element in a first wavelength range in which an absorption by the dry test element takes place which is previously known and is not equal to zero. A first correction value is determined from this absorption. The test element is subsequently irradiated after sample application and detection of the light reflected or transmitted from the test element in the first wavelength range in which an analyte-independent absorption by the wet test element takes place. A second correction value due to this change in light intensity is registered. Subsequently or before carrying out the second step of the method, the wet test element is irradiated and the light reflected or transmitted from the test element is detected in a second wavelength range in which an absorption by an analyte takes place. Hence the measured value is detected.

The first correction value is used to determine the amount of light that is registered by the detector despite an essentially complete absorption of the test element. If the dry test element has an essentially complete absorption in the first wavelength range, the detected correction value corresponds to the black value of the system. In the case of a previously known but essentially incomplete absorption of the dry test element, the black value is calculated by means of the evaluation unit. The second correction value gives the sum of the light intensity changes due to the previously known absorption of the dry test element and the sample-dependent, analyte-independent absorption. The sample-dependent portion of the light intensity changes is separated from the apparatus-related portion by subtracting the correction values. Subsequently the analyte concentration is determined in the second wavelength range with a correction of the measured values taking into account the black value and the sample-dependent absorption.

Another method for analysing and correcting non-analyte-dependent light intensity changes is carried out according to the invention by irradiating a test element before or after sample application and detecting the light reflected or transmitted from the test element in a first wavelength range in which either an absorption by the dry test element takes place which is previously known and is not equal to zero and is used to determine a first correction value or the absorption by the wet test element is detected in order to determine a second correction value. In this case the first correction value is used to determine the black value as already described. The second correction value additionally encompasses changes in light intensity which are the result of an influence of the sample. Subsequently or also before determining the second correction value, the test element is irradiated and the light reflected or transmitted from the test element is detected in a second wavelength range in which an absorption by an analyte takes place in order to determine the measured value. The analyte concentration is subsequently determined with the correction of the measured value taking into account the first or second correction value such that either only the black value of the method is taken into consideration or additionally the influence of sample.

The already described preferred embodiment result from both methods and hence it is possible to additionally determine the white value preferably on the basis of an analyte-free test element. Test elements with the described properties and in particular light-conducting properties can be used similarly to the system described above.

If the sample-dependent light intensity change in the first wavelength range is essentially equal to the sample-dependent light intensity change in the second wavelength range, determination of a correction value in the first wavelength range is sufficient and hence the latter method is preferred for correcting the measured value. If this is not the case, the sample-dependent absorption in the first wavelength range can be determined preferably in a further process step according to the first-mentioned method and used to determine the sample-dependent absorption in the second wavelength range.

Some calculation steps are illustrated in the following as an example.

If light in a first wavelength range is beamed onto a dry test element which has a previously known absorption ($I_{abs}$) this yields a theoretically expected measured value ($I_{theo}$) according to equation 1.

$$I_{theo} = I_{100\%} - I_{abs} \qquad (1)$$

in which ($I_{100\%}$) is a theoretically expected light intensity which is derived from the light emitted by the illumination unit when the analytical system behaves ideally. However, the light intensity ($I_{meas}$) that is actually detected comprises a light intensity change ($I_{app(1)}$) that results from inconstant conditions of the apparatus (e.g. variations in intensity due to ambient light, varying quality of the test strips, faulty coupling of the test strip to the illumination unit by the user, equation 2).

$$I_{meas} = I_{100\%} - I_{abs} - I_{app(1)} \qquad (2)$$

$I_{app}$ can be positive as well as negative.

If the previously known absorption ($I_{abs}$) of the test element is preferably essentially complete, the light is almost completely absorbed by the test element and the measured value ($I_{meas}$) is equal to the light intensity ($I_{app(1)}$) which is referred to within the scope of the invention as the first correction value. This correction value registers the light intensity that is analyte- and sample-independent and can a priori not be absorbed by the test element. Under the conditions that the measured value ($I_{meas}$) is equal to the correction value ($I_{app(1)}$), the measured value ($I_{meas}$) is referred to as the black value. Hence the black value gives the minimum light intensity that is registered by the detector despite an almost complete absorption of the test element.

In order to correct the measured value ($I_{analyte}$) when determining an analyte concentration in a second wavelength range, the black value ($I_{app(1)}$) is subtracted from the measured value ($I_{analyte}$) (equation 3).

$$I_{correction} = I_{analyte} - I_{app(1\ or\ 2)} \qquad (3)$$

If a second correction value is measured in the first wavelength range after applying sample to a test element where there is an essentially complete absorption by the test element, the correction value ($I_{app(2)}$) also includes those changes in light intensity that are caused by the analyte-independent influence of the sample (e.g. absorption by sample components, change in the refractive index on the test element) in addition to changes in light intensity due to the apparatus. If a correction value is only measured on the wet test element, the measured value ($I_{analyte}$) is also corrected by subtraction analogously to equation 3 when determining an analyte concentration.

In order to separate the sample-dependent portion of the light intensity change in the first wavelength range from the apparatus-dependent portion, a first correction value is determined before sample application and preferably before determining the second correction value. The sample-dependent changes in light intensity in the first wavelength range can be exclusively determined by subtracting the correction values.

The influence of sample in the second wavelength range can be deduced from the sample-dependent changes in light intensity in the first wavelength range.

In addition a comprehensive correction of the measured value ($I_{analyte}$) when determining an analyte concentration can additionally take a white value into account. In this case the white value is determined in a wavelength range in which the test element essentially does not absorb. Hence the white value gives the maximum light intensity that is registered by the detector.

For example it is possible to determine a first correction value and a white value ($I_{white}$) of the analytical system before sample application and to measure a second correction value after sample application. For this the first correction value is firstly determined in the first wavelength range. Subsequently a measurement is carried out in the second wavelength range in which there is almost no absorption by the test element so that the white value is registered.

The sample is applied to the test field which initiates a reaction of the analyte to be determined with a reagent. After the reaction is completed, a new measurement is carried out in the second wavelength range which now detects the analyte-dependent absorption.

A measurement in the first wavelength range is again repeated in order to register the second correction value. In the case of a previously known, essentially complete absorption by the dry test element, the first correction value corresponds to a black value which is sample- and analyte-independent. The second correction value corresponds to a black value which is analyte-independent. The sample-dependent light intensity change ($I_{sample}$) in the first wavelength range is obtained by subtracting the black values. The sample-dependent change in light intensity in the second wavelength range ($I'_{sample}$) is deduced from the sample-dependent light intensity change in the first wavelength range.

A correction value ($I_{correction}$) is determined according to equation 4.

$$I_{correction} = \frac{I_{analyte} - I_{app(1)} - I'_{sample}}{I_{white}} \qquad (4)$$

The determination of the correction values also allows the measurement to be terminated by the evaluation unit when the difference between the correction values exceeds a certain amount (X) (equation 5).

$$|I_{app(1)} - I_{app(2)}| \geq X \qquad 5)$$

Hence a deviation from the target value which is too large prevents the output of analytical results. This is for example the case when the test element has been soiled too strongly by sample application or has been damaged by the sample application.

The invention also concerns a test element having light-conducting properties for applying and analysing samples. The test element contains an absorber e.g. tartrazine which has a previously known absorption that is not equal to zero in a first wavelength range in which essentially no absorption due to an analyte takes place and the said absorption is essentially complete in a preferred embodiment. The substance does not interact with the sample. The test element also comprises a reagent system which reacts with the analyte of the sample in such a manner that an analyte-dependent change in the absorption takes place in a second wavelength range.

In an advantageous embodiment the substance absorbs in the blue wavelength range. There is preferably essentially no absorption by the test element in the second or a third wavelength range. Other preferred embodiments are derived as already described and are shown in the figures.

FIG. 1: Analytical system with test element.

Figure 2:
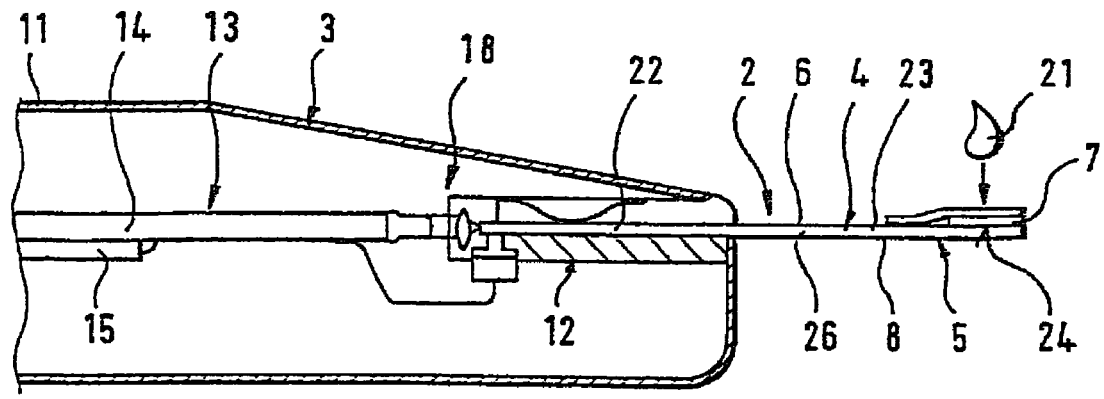

FIG. 2: Design of an analytical system with a light-conducting test element corresponding to the patent application WO 01/48464.

FIG. 3: Design of a light-conducting test element corresponding to the patent application WO 01/48464.

The analytical system 1 shown in FIGS. 1 and 2 comprises a test element (2) and an evaluation device (3). The test element (2) is designed as a test strip (4) with an elongate support foil (5) made of plastic and a test field (7) attached to the upper flat side (6) of the support foil (5).

The test element (2) is inserted into a test element holder (12) through an opening (10) in the housing (11) of the evaluation device (3) and thus positioned in the measuring position shown in FIG. 2. The evaluation device (3) contains measuring and evaluation electronics 13 which in the case shown are in the form of a circuit board (14) and integrated circuits (15). A light emitter (16) preferably in the form of a light emitting diode (LED) and a detector (17) preferably in the form of a photodiode which are components of an optical measuring device (18) are connected to the measuring and evaluation electronics (13).

In order to carry out an analysis, a drop of sample liquid (21) is applied to the side (upper side) of the test field (7) which faces away from the support foil (5). Sample application is facilitated by the fact that only a first section (22) of the test element (2) positioned in the measuring position is located inside the housing (11) whereas a second section (23) containing the test field (7) protrudes from the housing (11) and is thus readily accessible. The liquid penetrates while dissolving the reagents contained in the test field (7) until it reaches the detection zone (24) which is located on the side (underside) of the test field (7) which faces towards the support foil (5).

The reaction of the analyte contained in the sample with the reagent system results in an optically measurable change and in particular a color change of the detection zone (24). The intensity of the diffusely reflected secondary light is measured for the photometric evaluation when the detection zone (24) is illuminated with primary light. This is a result of a special design of the test element (2) and interacting parts of the optical measuring device (18).

FIG. 3 shows a test element with light-conducting elements.

The support foil (5) includes at least one optical light-conducting layer (26) having the above-mentioned properties with regard to optical transparency and refractive index. Further information on light-conductors whose light transport is based on total reflection is given by the relevant literature. (WO 01/48461).

The support foil (5) has two light-conducting layers (26) where the upper light-conducting layer serves as the primary light conductor (27) and the lower light-conducting layer serves as the secondary light conductor (28). The primary light (29) is coupled by the light emitter (16) with the aid of a lens (30) into the primary light conductor (27) through its end face which serves as an entry face (31) for the coupling and is transported within the primary light conductor (27) to the test field (7). The portion of the light path of the primary light (29) which runs in the interior of the light-conducting layer (26) is referred to as the light-conducting section (32). The area of the upper flat side (6) of the light-conducting layer (26) which is in alignment with the test field is used at least partly as an area where light is coupled out (33) in that primary light (29) is coupled out of the primary light conductor (27) into the detection zone (24) of the test field (7).

In the embodiment shown the primary lights (29) is essentially coupled out by the fact that the lower flat side of the support foil (5) which is opposite to the coupling-out area (33) (i.e. also opposite to the test field (7)) (in the case of the two layer embodiment of the support foil: the lower flat side of the primary light conductor (27)) is designed such that the primary light is deflected into the detection zone (24) of the test field (7). This change in the direction of light propagation is effected by a reflecting surface (25) which is preferably tilted below an angle of ca. 45°. In order to improve its reflective properties it should be polished and/or provided with a metallic shiny coating. Deviations from the angle of 45° are possible.

The invention claimed is:

1. Analytical system for determining an analyte in which non-analyte-dependent light intensity changes are taken into account comprising
   a test element having an absorption of light in a first wavelength range which is previously known and is not equal to zero,
   an illumination unit configured and arranged to emit radiation in the first wavelength range and in a second wavelength range, and configured and arranged within the system to irradiate the test element,
   a detector unit which is positioned in such a manner that light transmitted or reflected by the test element is registered,
   an evaluation unit configured and arranged within the system to receive signals from the detector when it is irradiated, the evaluation unit being further configured to (i) determine a correction value from an absorption of the test element in the first wavelength range before sample application, (ii) determine a measured value in the second wavelength range wherein the measured value in the second wavelength range is dependent on the analyte concentration after sample application on the test element, and (iii) determine the concentration of the analyte from the measured value taking into account the correction value.

2. System as claimed in claim 1 wherein the evaluation unit is further configured to register at least two correction values in the first wavelength range.

3. System as claimed in claim 1 wherein the test element comprises a light-conducting element in cooperative arrangement with the illumination unit within the system.

4. System as claimed in claim 1 wherein the test element comprises an absorber which does not interact with the sample, the absorber being configured to establish the known absorption of the test element.

5. System as claimed in claim 1, in which the previously known absorption is essentially complete.

6. System as claimed in claim 1, the illumination unit being further configured and arranged to emit radiation in a third wavelength range, the test element further having an absorption of light in the third wavelength range of essentially zero, wherein the evaluation unit is further configured and arranged to determine a white value comprising a light intensity of the test element in the third wavelength range before sample application and to correct the measured value taking into account the white value.

7. System as claimed in claim 1, the test element further having an absorption of light in the second wavelength range of essentially zero, wherein the evaluation unit is further configured and arranged to determine a white value comprising a light intensity of the test element in the second wavelength range before sample application and to correct the measured value taking into account the white value.

8. System as claimed in claim 7 in which the test element has essentially no absorption in the second wavelength range before sample application.

9. Method for analysing and correcting non-analyte-dependent changes in light intensity comprising the steps (a) irradiating a test element before sample application and detecting the light reflected or transmitted by the test element in a first wavelength range in which an absorption by the test element to which the sample has not been added takes place which is previously known and is not equal to zero and determining a first correction value based on the detected light, (b) irradiating the test element after adding the sample and detecting the light reflected or transmitted by the test element in the first wavelength range in which the previously known absorption of the dry test element and an analyte-independent, sample-dependent light intensity change takes place and determining a second correction value based on the detected light, subsequently or before method step (b), irradiating the test element and detecting the light reflected or transmitted by the test element in a second wavelength range in which an absorption by an analyte takes place and determining the measured value computing for the first and second correction value in order to determine the proportion of the light intensity changes that are due to the sample, determining the amount of light (black value) that is registered by the detector when there is an essentially complete absorption of the dry test element using the first correction value, calculating the analyte concentration in the second wavelength range with a correction of the measured value taking into account the black value and the sample-dependent change in light intensity.

10. Method as claimed in claim 9 in which the dry test element essentially completely absorbs.

11. Method as claimed in claim 9 in which the sample-dependent change in light intensity in the first wave-length range is set as essentially equal to the sample-dependent change in light intensity in the second wavelength range.

12. Method as claimed in claim 9 in which the sample-dependent change in light intensity in the second wavelength range is determined on the basis of the sample-dependent change in light intensity in the first wavelength range.

13. Method as claimed in claim 9 in which a value is determined using the first and the second correction value and a signal is generated as soon as the value deviates by a predetermined extent from a target value.

14. Method as claimed in claim 9 in which the test element is irradiated in the second or in a third wavelength range in which essentially no absorption by the test element takes place (white value) and the measured value is corrected taking into account the white value.

15. Method as claimed in claim 14 in which the white value is measured in the second wavelength range before sample application.

16. Method for analysing and correcting non-analyte-dependent changes in light intensity comprising the steps irradiating a test element in a first wavelength range before and after sample application where the test element has an absorption in the first wavelength range before sample application which is previously known and is not equal to zero, detecting the light reflected or transmitted by the test element in the first wavelength range and determining a first and a second correction value based on the detected light, irradiating the test element after sample application and detecting the light reflected or transmitted by the test element in a second wavelength range in which an absorption by an analyte takes place and determining the measured value, determining the analyte concentration with a correction of the measured value taking into account the first or second correction value.

17. Method as claimed in claim 16 in which the dry test element essentially completely absorbs.

18. Method as claimed in claim 16 in which the test element is irradiated in the second or in a third wavelength range in which essentially no absorption by the test element takes place (white value) and correcting the measured value taking into account the white value.

19. Method as claimed in claim 18 in which the white value is measured in the second wavelength range before sample application.

* * * * *